US011785348B2

(12) United States Patent
Choi et al.

(10) Patent No.: US 11,785,348 B2
(45) Date of Patent: Oct. 10, 2023

(54) ENDOSCOPIC REFLECTION MICROSCOPE USING OPTICAL FIBER BUNDLE AND IMAGE ACQUISITION METHOD USING THE SAME

(71) Applicants: Korea University Research and Business Foundation, Seoul (KR); Institute for Basic Science, Daejeon (KR)

(72) Inventors: Won Shik Choi, Seoul (KR); Won Jun Choi, Seoul (KR); Mun Kyu Kang, Seoul (KR)

(73) Assignees: Korea University Research and Business Foundation, Seoul (KR); Institute for Basic Science, Daejeon (KR)

( * ) Notice: Subject to any disclaimer, the term of this patent is extended or adjusted under 35 U.S.C. 154(b) by 265 days.

(21) Appl. No.: 17/484,189

(22) Filed: Sep. 24, 2021

(65) Prior Publication Data
US 2022/0103733 A1    Mar. 31, 2022

(30) Foreign Application Priority Data
Sep. 25, 2020   (KR) .......................... 10-2020-0124780

(51) Int. Cl.
*G02B 23/24*   (2006.01)
*H04N 23/75*   (2023.01)
(Continued)

(52) U.S. Cl.
CPC .............. *H04N 23/75* (2023.01); *A61B 1/04* (2013.01); *A61B 1/07* (2013.01); *G01N 21/954* (2013.01);
(Continued)

(58) Field of Classification Search
CPC ........ H04N 23/75; H04N 23/555; A61B 1/04; A61B 1/07; A61B 5/0071;
(Continued)

(56) References Cited

U.S. PATENT DOCUMENTS 10,571,678 B2 * 2/2020 Andresen ........... G02B 21/0004
2005/0174425 A1 * 8/2005 Harris ................ G02B 21/0076
348/45
(Continued)

FOREIGN PATENT DOCUMENTS

JP    2015-19862 A    2/2015
JP    6651032 B2      2/2020
(Continued)

OTHER PUBLICATIONS

Kang, Sungsam et al. "High-Resolution Adaptive Optical Imaging within Thick Scattering Media using Closed-Loop Accumulation of Single Scattering." *Nature communications* vol. 8 No. 1, 2017 pp. 1-10.
(Continued)

*Primary Examiner* — Howard D Brown, Jr.
(74) *Attorney, Agent, or Firm* — NSIP Law

(57) ABSTRACT

Disclosed are an endoscopic reflection microscope using an optical fiber bundle and an image acquisition method using the same. The endoscopic reflection microscope includes an incident wave output unit configured to output an incident wave to a target object through any one optical fiber in an optical fiber bundle, a reflected wave receiver configured to receive a reflected wave output from the target object in response to the incident wave through a plurality of corresponding optical fibers in the optical fiber bundle, and an image acquirer configured to establish a reflection matrix corresponding to the reflected wave and to acquire an image in which at least one of phase retardation of the incident
(Continued)

wave or phase retardation of the reflected wave is compensated for based on the established reflection matrix.

11 Claims, 18 Drawing Sheets

(51) Int. Cl.
*A61B 1/07* (2006.01)
*A61B 1/04* (2006.01)
*G02B 21/00* (2006.01)
*G01N 21/954* (2006.01)
*G02B 23/26* (2006.01)
*H04N 23/50* (2023.01)

(52) U.S. Cl.
CPC ..... *G02B 21/0028* (2013.01); *G02B 23/2484* (2013.01); *G02B 23/26* (2013.01); *G01N 2021/9546* (2013.01); *H04N 23/555* (2023.01)

(58) Field of Classification Search
CPC .......... A61B 1/000095; A61B 1/00167; A61B 5/0068; A61B 5/0084; A61B 1/00009; A61B 1/00057; A61B 1/00188; G01N 21/954; G01N 2021/9546; G02B 21/0028; G02B 23/2484; G02B 23/26; G02B 21/0032
See application file for complete search history.

(56) References Cited

U.S. PATENT DOCUMENTS

| 2006/0211915 | A1* | 9/2006 | Takeuchi ................. A61B 1/05 600/109 |
| 2012/0283516 | A1* | 11/2012 | Kang ................... A61B 1/0623 600/182 |
| 2017/0167980 | A1* | 6/2017 | Dimitriadis .......... A61B 5/0071 |
| 2019/0129026 | A1* | 5/2019 | Sumi ................... G01S 15/8915 |
| 2021/0382290 | A1* | 12/2021 | Rigneault .......... A61B 1/00172 |

FOREIGN PATENT DOCUMENTS

| KR | 10-2008-0098248 A | 11/2008 |
| KR | 10-2013-0080940 A | 7/2013 |
| KR | 10-1502236 B1 | 3/2015 |
| KR | 10-2016-0028557 A | 3/2016 |
| KR | 10-1822671 B1 | 1/2018 |
| KR | 10-2020-0004318 A | 1/2020 |

OTHER PUBLICATIONS

Korean Office Action dated Nov. 23, 2021 in corresponding Korean Patent Application No. 10-2020-0124780 (6 pages in Korean).

* cited by examiner

[FIG. 1]
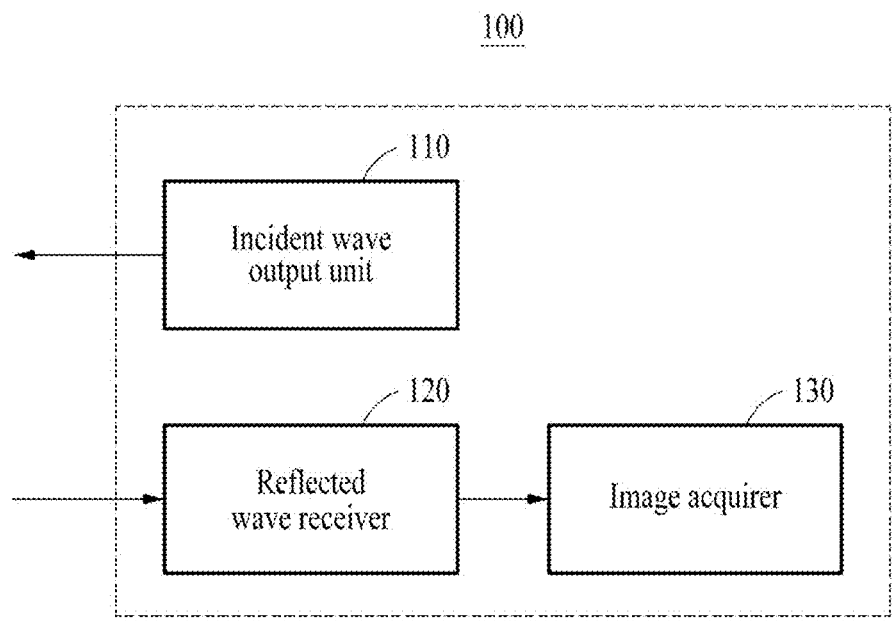
[FIG. 2A]
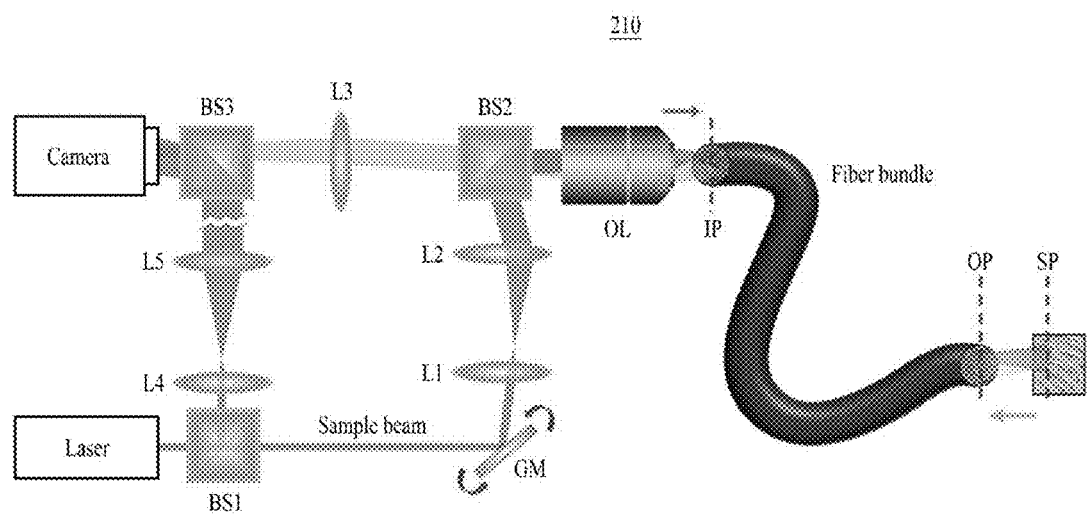

[FIG. 2B]
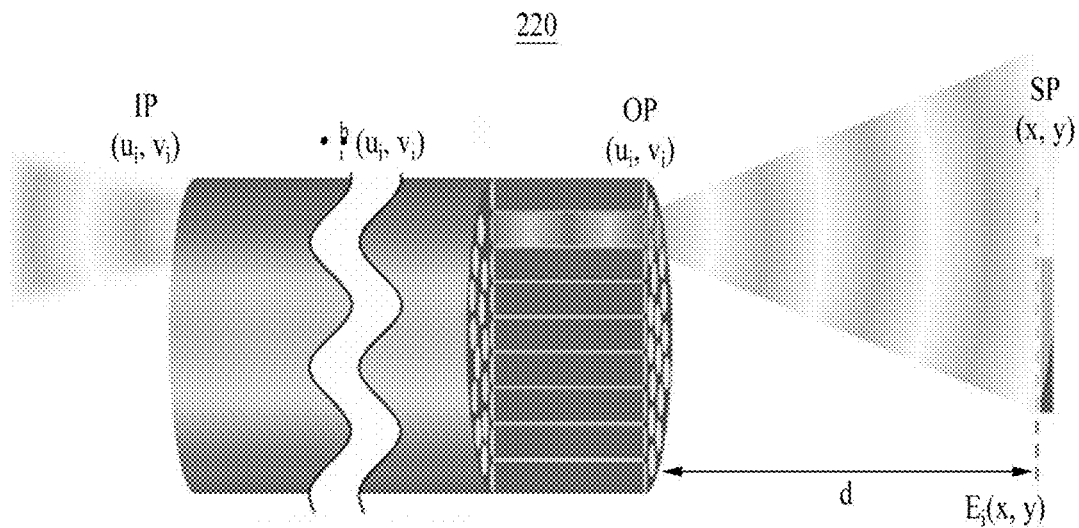
[FIG. 2C]
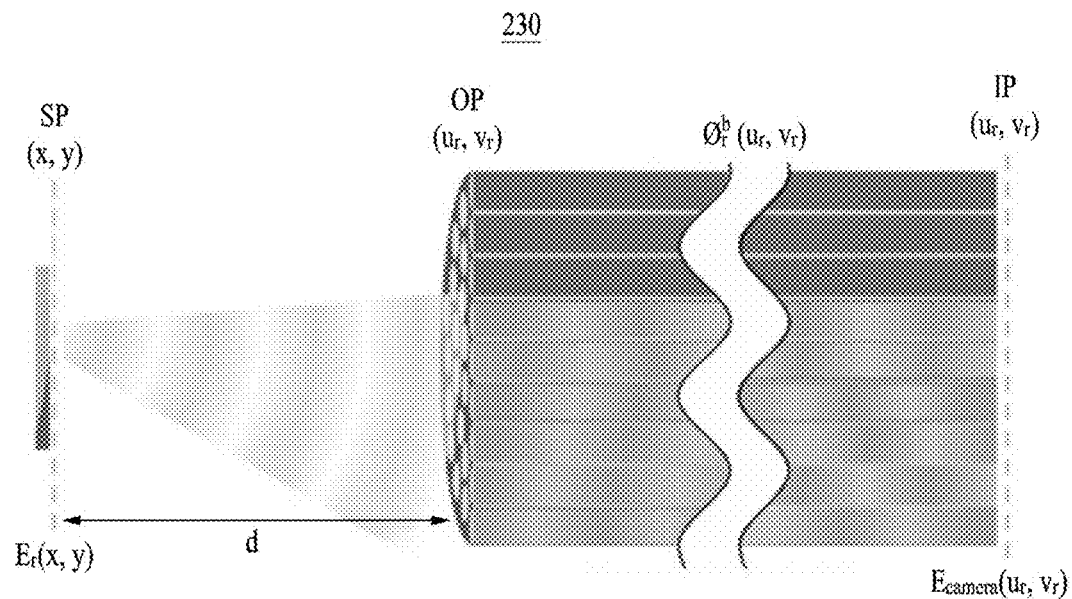

[FIG. 3]
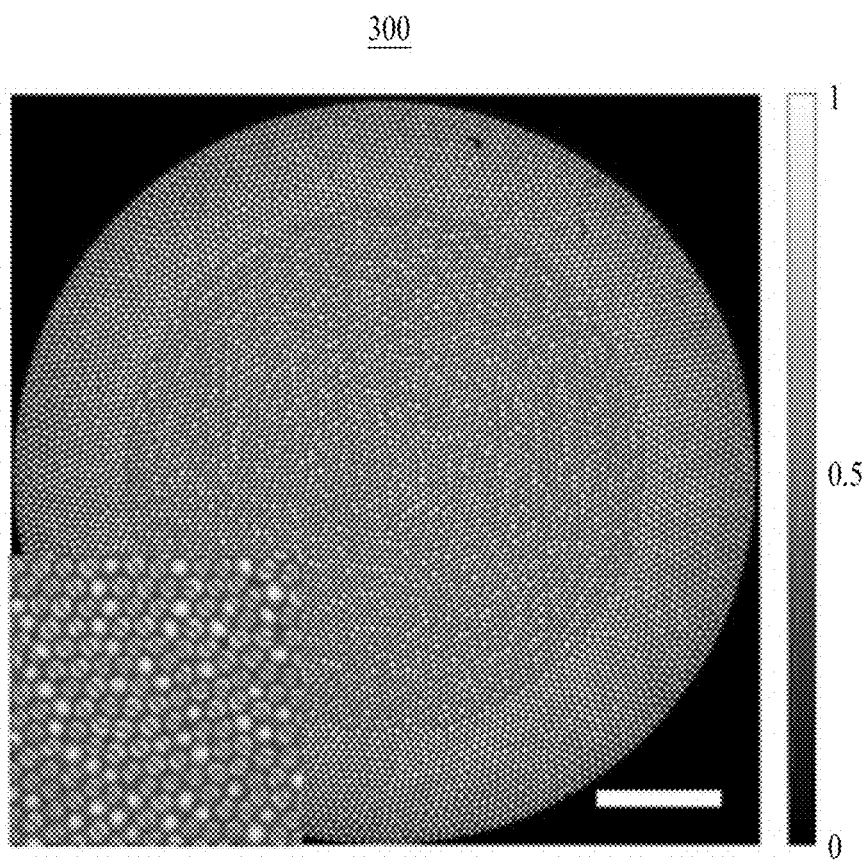

[FIG. 4A]
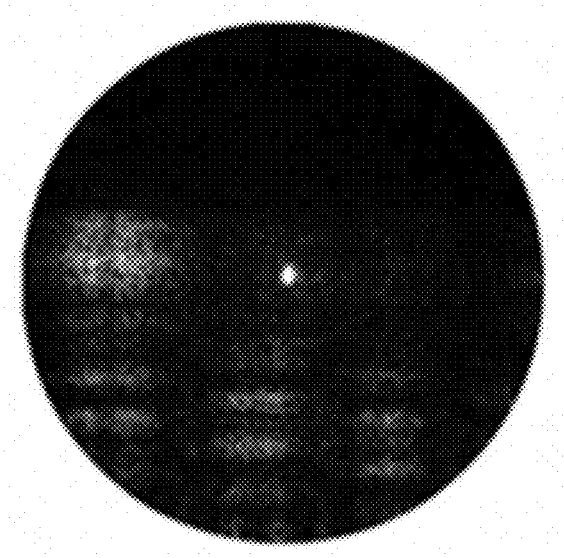
[FIG. 4B]

[FIG. 4C]
[FIG. 4D]
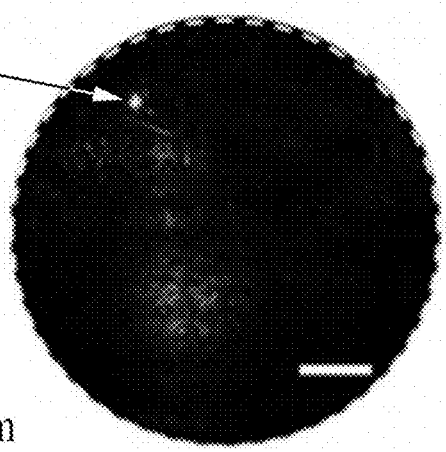

[FIG. 4E]
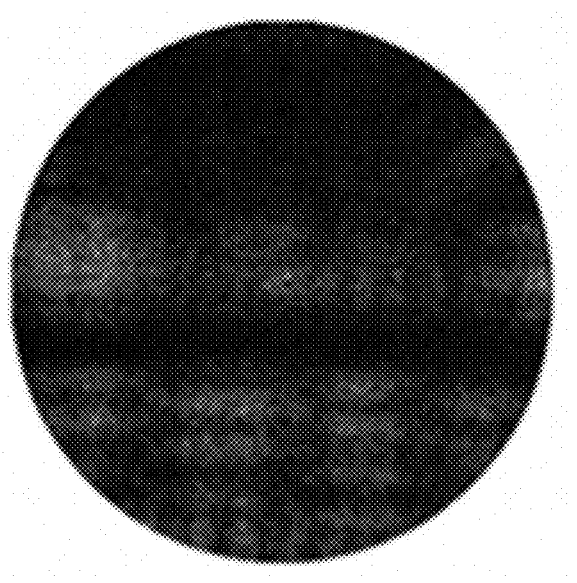
[FIG. 4F]
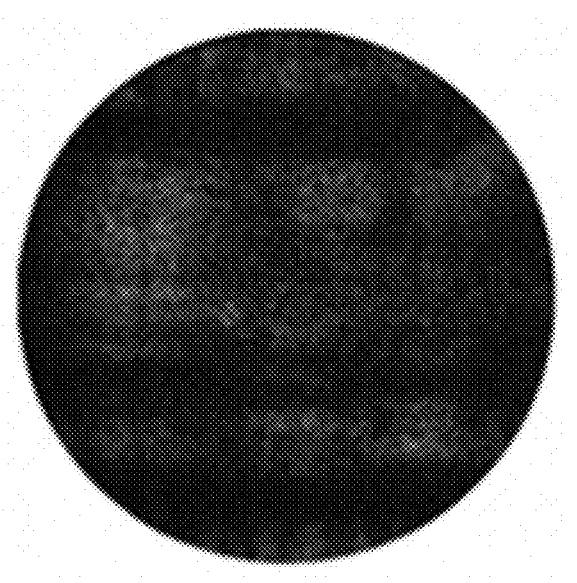

[FIG. 4G]
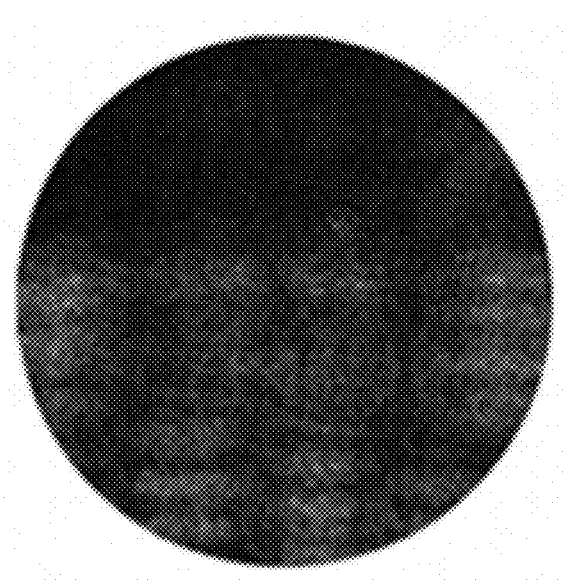
[FIG. 4H]
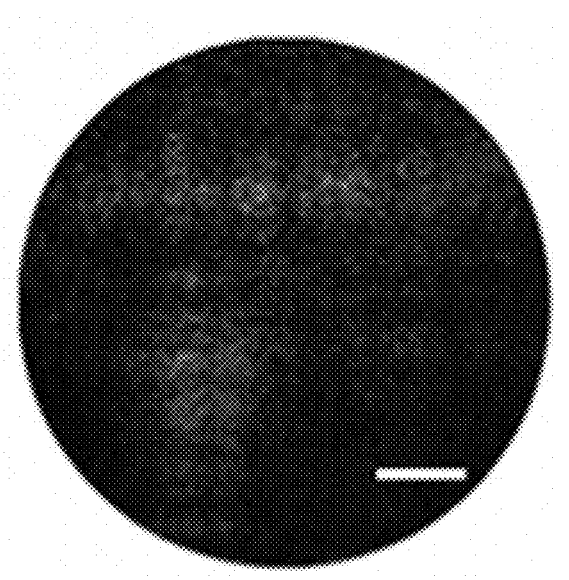

[FIG. 5A]
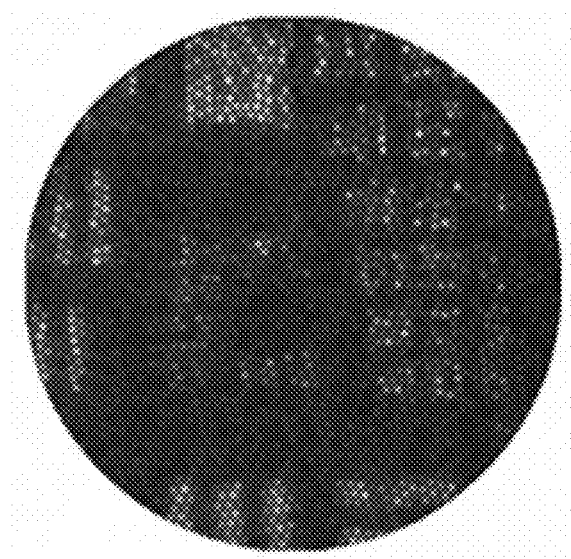
[FIG. 5B]
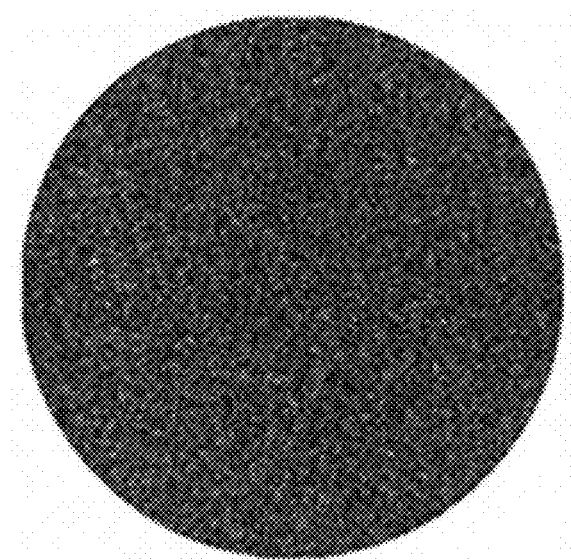

[FIG. 5C]
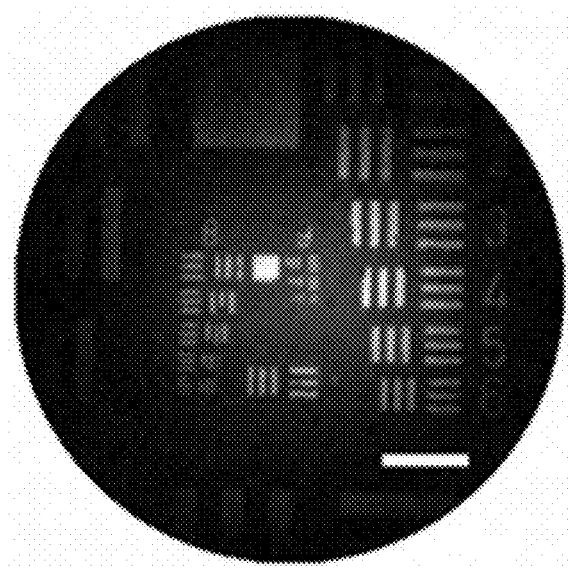
[FIG. 5D]
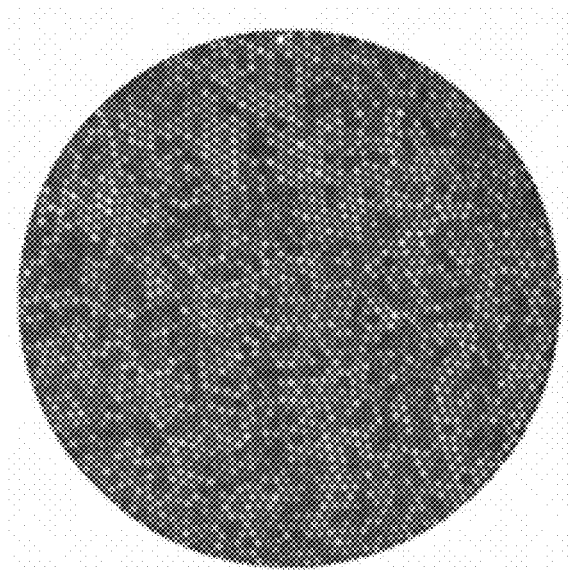

[FIG. 5E]
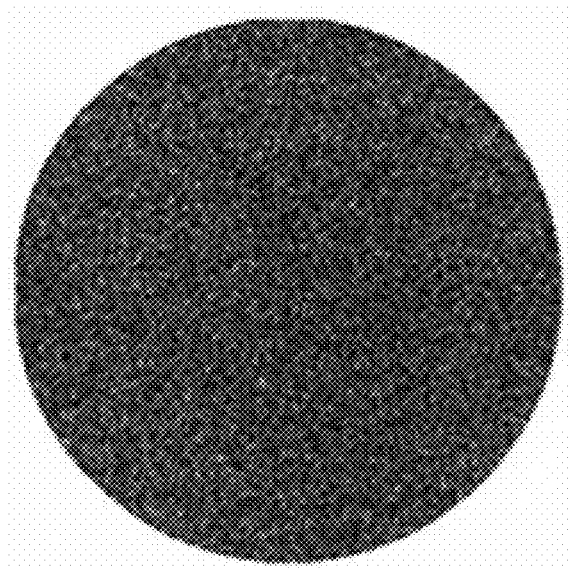
[FIG. 5F]
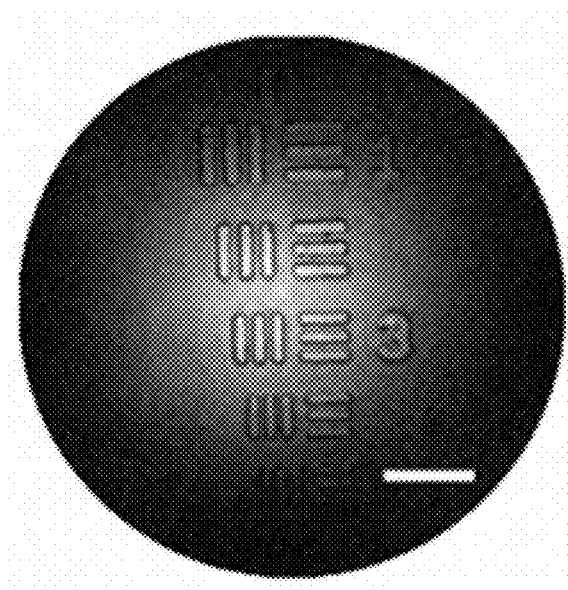

[FIG. 6A]
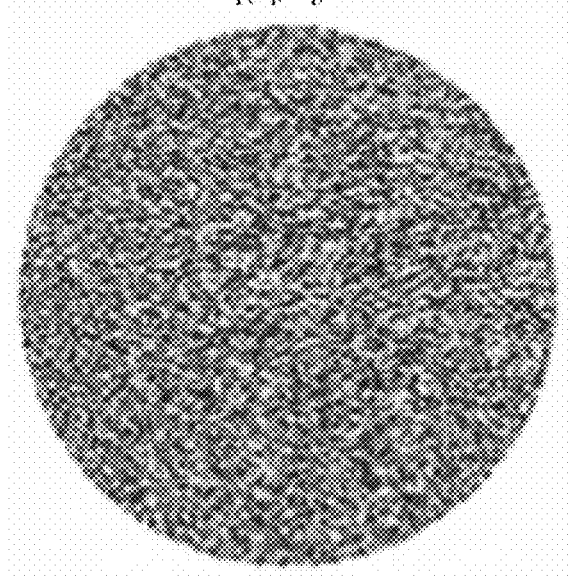
$\emptyset_i(u_i, v_i)$
[FIG. 6B]
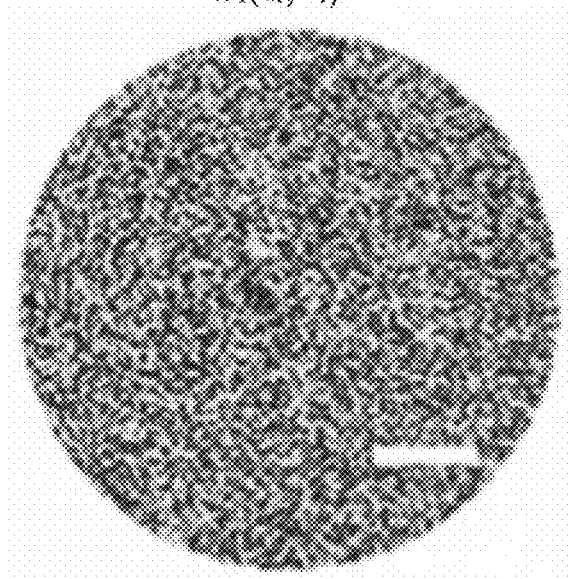
$\emptyset_r(u_r, v_r)$

[FIG. 6C]
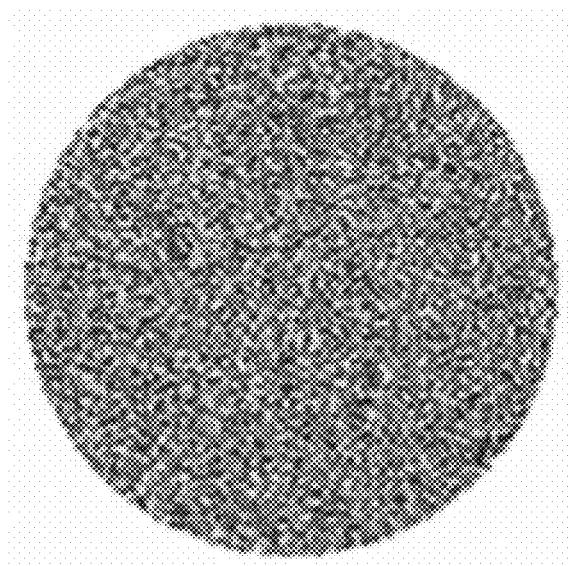
[FIG. 6D]
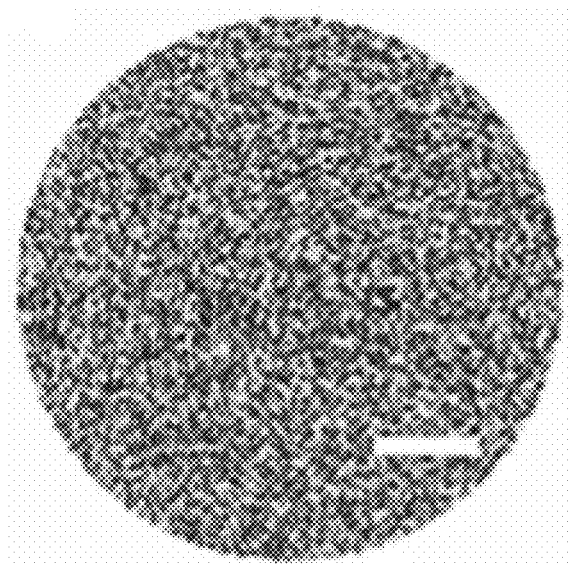

[FIG. 7A]
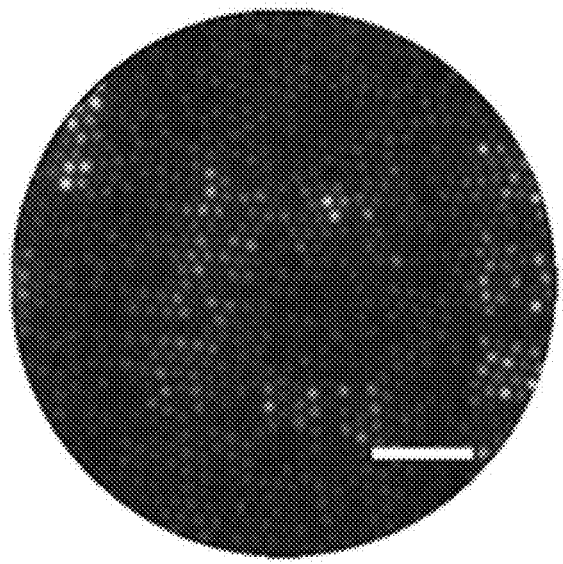
[FIG. 7B]
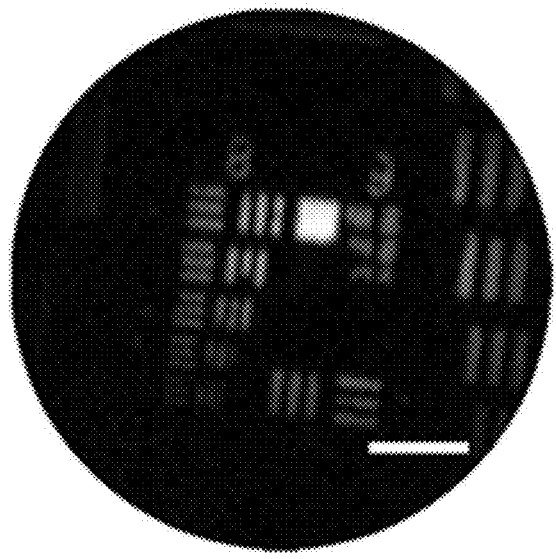

[FIG. 8]
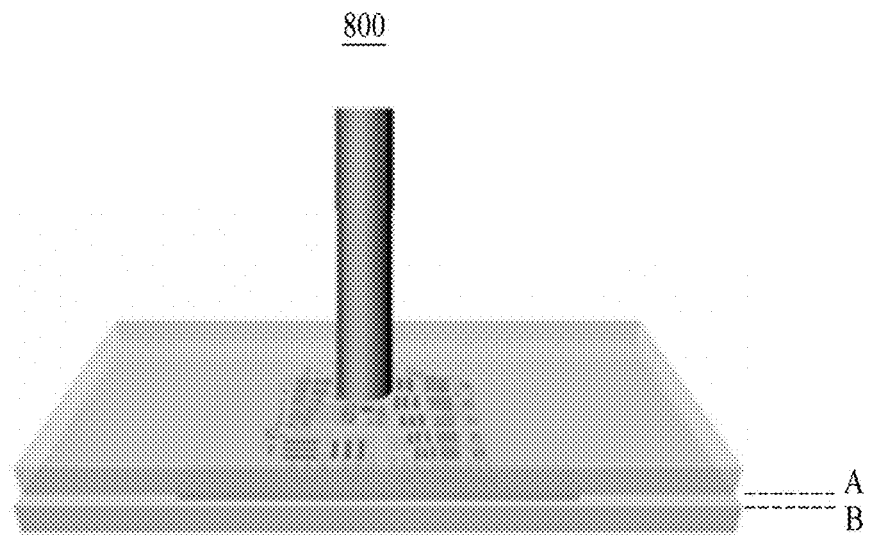
[FIG. 9A]
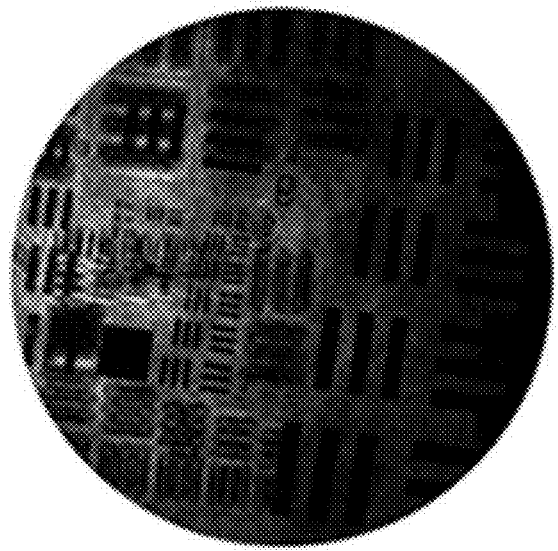

[FIG. 9B]
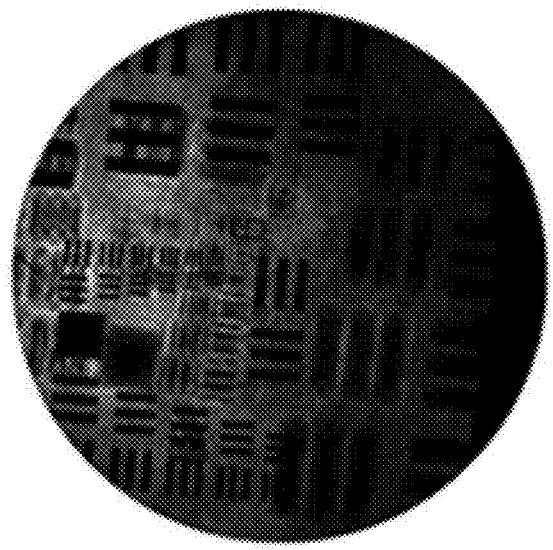
[FIG. 9C]
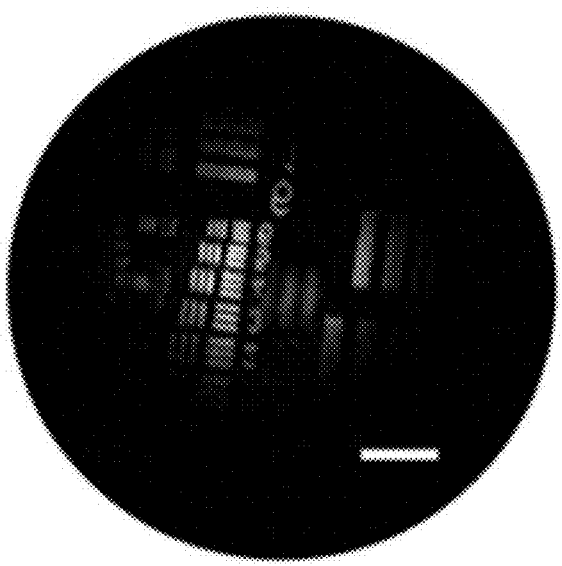

[FIG. 9D]
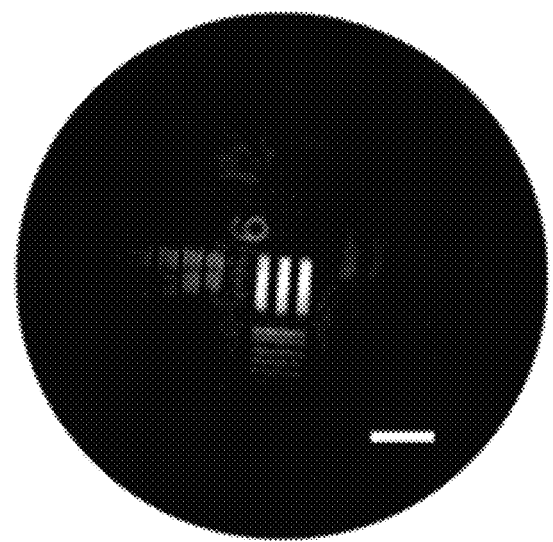
[FIG. 10A]
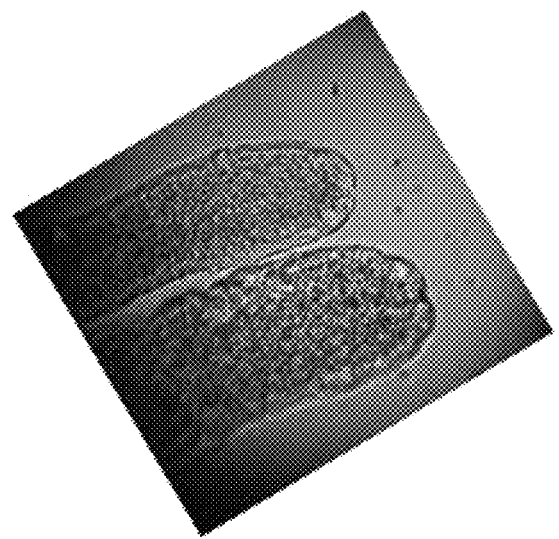

[FIG. 10B]
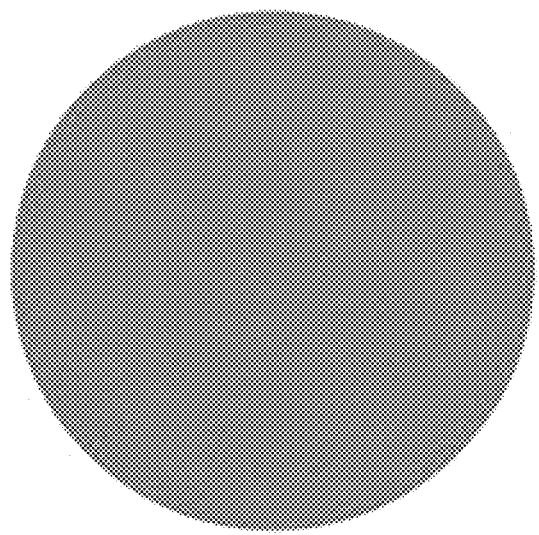
[FIG. 10C]
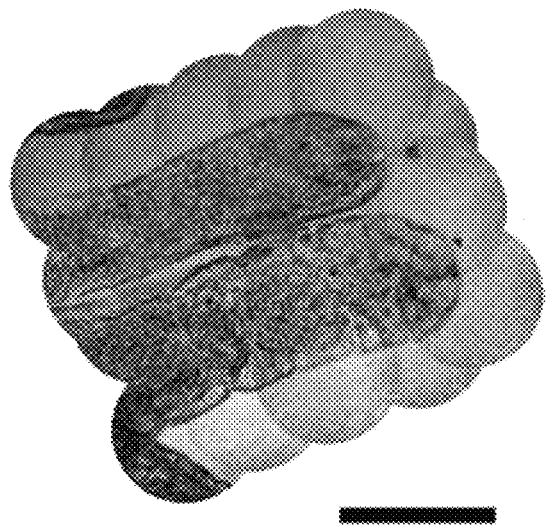
Scale bar 100 micron

[FIG. 11]
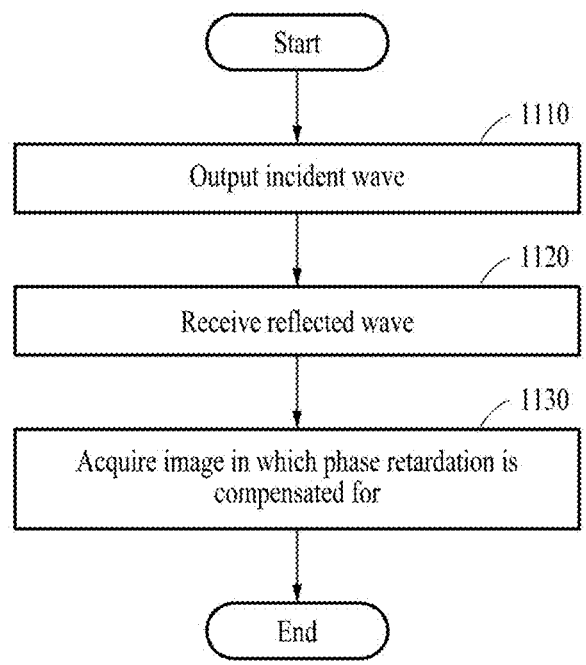

ENDOSCOPIC REFLECTION MICROSCOPE USING OPTICAL FIBER BUNDLE AND IMAGE ACQUISITION METHOD USING THE SAME

CROSS-REFERENCE TO RELATED APPLICATION

This application claims priority to and the benefit of Korean Patent Application No. 2020-0124780, filed on Sep. 25, 2020, the disclosure of which is incorporated herein by reference in its entirety.

BACKGROUND OF THE INVENTION

1. Field of the Invention

The present disclosure relates to an endoscopic reflection microscope and an image acquisition method using the same, and more particularly to a technological idea for acquiring an image in which phase retardation is compensated for in an endoscopic reflection microscope including an optical fiber bundle-based probe.

2. Description of the Related Art

An endoscopic reflection microscope including a very thin probe based on optical fibers is capable of acquiring an image of an area that a conventional optical system has difficulty in accessing, such as the inside of the human body, and thus various research has been conducted into related fields, but there are various technical limitations in acquiring high-resolution images using elastically scattered light.

In the case of an endoscopic microscope using an optical fiber bundle, some of incident light injected into the optical fiber to illuminate an object is internally reflected at an end of the optical fiber and interferes with light reflected from the object, thereby distorting an image of the object.

Accordingly, in order to separate two light beams, a non-linear image using fluorescence or two-photon phenomenon is acquired, and in this regard, each optical fiber in the optical fiber bundle is used as a pixel of an image, and thus there is a problem in that the resolution of the image is limited by an interval between cores of optical fibers and it is impossible to use the endoscopic microscope to observe and diagnose the human body.

When an image is acquired through an optical fiber, a plurality of spatial modes corresponding to the amount of information on the image is required. Thus, single-mode optical fibers employ a mechanical scanning process to acquire image information.

A multi-mode based endoscopic microscope using a transmission matrix and an optical fiber previously measures a transmission matrix with the transmission characteristics of a multi-mode optical fiber and restores image information transmitted through the multi-mode optical fiber using the transmission matrix. However, there is a problem in that it is possible to apply the technology only to a multi-mode optical fiber of a fixed shape that does not change because the transmission matrix needs to be measured again whenever a curved shape of the multi-mode optical fiber is changed.

CITED REFERENCE

Patent Document

U.S. patent Ser. No. 10/571,678, "Device and method for controlling group velocity delays of pulses propagating in mono mode optical fibers of a fiber bundle"

Japanese Patent No. 6651032, "Fiber optic system and method of operating fiber optic system"

Korean Patent No. 10-1502236, "3D multicolor fluorescence confocal microscope and method of generating information on depth of test piece using the same"

Non-Patent Document

"High-resolution adaptive optical imaging within thick scattering media using closed-loop accumulation of single scattering", Nature Communications volume 8, Article number: 2157, 2017

SUMMARY OF THE INVENTION

Therefore, the present disclosure has been made in view of the above problems, and it is an object of the present disclosure to provide an endoscopic reflection microscope and an image acquisition method using the same for compensating for phase retardation due to an optical fiber bundle in real time without a pre-calibration process.

It is another object of the present disclosure to provide an endoscopic reflection microscope and an image acquisition method using the same for acquiring an image from which a back-reflection noise component is removed.

It is a further object of the present disclosure to provide an endoscopic reflection microscope and an image acquisition method using the same for acquiring an image in which phase retardation due to the optical fiber bundle is compensated for by accessing the inside of a precision machine or the inside of the human body that a conventional microscope has difficulty in accessing, through an optical fiber bundle-based probe.

It is yet another object of the present disclosure to provide an endoscopic reflection microscope and an image acquisition method using the same for providing a high-resolution image using a reflected wave having the same wavelength as an incident wave without any dyeing for two-photon or fluorescence measurement.

In accordance with an aspect of the present disclosure, the above and other objects can be accomplished by the provision of an endoscopic reflection microscope comprising: an incident wave output unit configured to output an incident wave to a target object through any one optical fiber in an optical fiber bundle; a reflected wave receiver configured to receive a reflected wave output from the target object in response to the incident wave through a plurality of corresponding optical fibers in the optical fiber bundle; and an image acquirer configured to establish a reflection matrix corresponding to the reflected wave and to acquire an image in which at least one of phase retardation of the incident wave or phase retardation of the reflected wave is compensated for based on the established reflection matrix.

In accordance with an aspect, the target object may be spaced apart from an emitting surface of the optical fiber bundle by a distance of 400 µm to 1,200 µm.

In addition, the image acquirer may distinguish a raw image corresponding to the reflected wave between a plurality of pixels on which a reflection data component is concentrated and a pixel on which a back-reflection noise component is concentrated and may physically remove the back-reflection noise component from the pixel on which the back-reflection noise component is concentrated.

In accordance with an aspect, the image acquirer may derive a complex field-map based on the raw image corresponding to the reflected wave and may establish the reflection matrix based on the complex field-map.

In accordance with an aspect, the reflection matrix may be a matrix including spatial coordinates of the incident wave and spatial coordinates of the reflected wave as a column index and a row index in the optical fiber bundle, respectively and having components of the complex field-map as matrix elements.

In accordance with an aspect, the image acquirer may acquire the image in which phase retardation is compensated for through correlation analysis based on the established reflection matrix.

In accordance with an aspect, the image acquirer may derive a phase retardation component of the incident wave through correlation analysis between columns of the established reflection matrix and may compensate for the phase retardation component of the incident wave in the complex field-map.

In accordance with an aspect, the phase retardation component of the incident wave may be a component obtained by performing calculation of a scaling factor and the spatial coordinate component of the incident wave on a core-dependent phase retardation component of the incident wave in the optical fiber bundle.

In accordance with an aspect, the image acquirer may derive a phase retardation component of the reflected wave through correlation analysis between rows of the established reflection matrix and may compensate for the phase retardation component of the reflected wave in the complex field-map in which the phase retardation component of the incident wave is compensated for.

In accordance with an aspect, the phase retardation component of the reflected wave may be a component obtained by performing calculation of a scaling factor and the spatial coordinate component of the reflected wave on a core-dependent phase retardation component of the reflected wave in the optical fiber bundle.

In accordance with an aspect, the image acquirer may derive the complex field-map through Hilbert transform on the raw image corresponding to the reflected wave.

In accordance with another aspect of the present disclosure, there is provided an image acquisition method using an endoscopic reflection microscope, the method comprising: outputting an incident wave to a target object through any one optical fiber in an optical fiber bundle, by an incident wave output unit; receiving a reflected wave output from the target object in response to the incident wave through a plurality of corresponding optical fibers in the optical fiber bundle, by a reflected wave receiver, and establishing a reflection matrix corresponding to the reflected wave and acquiring an image in which at least one of phase retardation of the incident wave or phase retardation of the reflected wave is compensated for based on the established reflection matrix, by an image acquirer.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 is a diagram for explaining an endoscopic reflection microscope according to an embodiment;

FIGS. 2A to 2C are diagrams for explaining an embodiment of an endoscopic reflection microscope according to an embodiment;

FIG. 3 is a diagram for explaining an example of outputting an incident wave through an optical fiber bundle according to an embodiment;

FIGS. 4A to 4H are diagrams for explaining an example of deriving a complex field-map through an endoscopic reflection microscope according to an embodiment;

FIGS. 5A to 5F are diagrams for explaining an example of acquiring an image through an endoscopic reflection microscope according to an embodiment;

FIGS. 6A to 6D are diagrams for explaining an example of identifying phase retardation through an endoscopic reflection microscope according to an embodiment;

FIGS. 7A to 7B are diagrams for explaining an example of acquiring an image of a target object positioned in a narrow and curved path using an endoscopic reflection microscope according to an embodiment;

FIG. 8 is a diagram for explaining an experimental process of acquiring an image by adjusting a focal length by an endoscopic reflection microscope according to an embodiment;

FIGS. 9A to 9D are diagrams for explaining an example of acquiring an image through the experimental process by an endoscopic reflection microscope according to an embodiment;

FIGS. 10A to 10C are diagrams for explaining an example of acquiring an image of biological tissue that is not dyed through an endoscopic reflection microscope according to an embodiment; and FIG. 11 is a diagram for explaining an image acquisition method using an endoscopic reflection microscope according to an embodiment.

DETAILED DESCRIPTION OF THE INVENTION

The present disclosure will now be described more fully with reference to the accompanying drawings, in which exemplary embodiments of the disclosure are shown.

This disclosure, however, should not be construed as limited to the exemplary embodiments and terms used in the exemplary embodiments, and should be understood as including various modifications, equivalents, and substituents of the exemplary embodiments.

Preferred embodiments of the present disclosure are now described more fully with reference to the accompanying drawings. In the description of embodiments of the present disclosure, certain detailed explanations of related known functions or constructions are omitted when it is deemed that they may unnecessarily obscure the essence of the disclosure.

In addition, the terms used in the specification are defined in consideration of functions used in the present disclosure, and can be changed according to the intent or conventionally used methods of clients, operators, and users. Accordingly, definitions of the terms should be understood on the basis of the entire description of the present specification.

In the drawings, like reference numerals in the drawings denote like elements.

As used herein, the singular forms "a," "an" and "the" are intended to include the plural forms as well, unless context clearly indicates otherwise.

Expressions such as "A or B" and "at least one of A and/or B" should be understood to include all possible combinations of listed items.

Expressions such as "a first," "the first," "a second" and "the second" may qualify corresponding components irrespective of order or importance and may be only used to distinguish one component from another component without being limited to the corresponding components.

In the case in which a (e.g., first) component is referred as "(functionally or communicatively) connected" or "attached" to another (e.g., second) component, the first component may be directly connected to the second component or may be connected to the second component via another component (e.g., third component).

In the specification, the expression " . . . configured to . . . (or set to)" may be used interchangeably, for example, with expressions, such as " . . . suitable for . . . ," " . . . having ability to . . . ," " . . . modified to . . . ," " . . . manufactured to . . . ," " . . . enabling to . . . ," or " . . . designed to . . . ," in the case of hardware or software depending upon situations.

In any situation, the expression "a device configured to . . . " may refer to a device configured to operate "with another device or component."

For examples, the expression "a processor configured (or set) to execute A, B, and C" may refer to a specific processor performing a corresponding operation (e.g., embedded processor), or a general-purpose processor (e.g., CPU or application processor) executing one or more software programs stored in a memory device to perform corresponding operations.

In addition, the expression "or" means "inclusive or" rather than "exclusive or".

That is, unless otherwise mentioned or clearly inferred from context, the expression "x uses a or b" means any one of natural inclusive permutations.

In the aforementioned embodiments, constituents of the present disclosure were expressed in a singular or plural form depending upon embodiments thereof.

However, the singular or plural expressions should be understood to be suitably selected depending upon a suggested situation for convenience of description, and the aforementioned embodiments should be understood not to be limited to the disclosed singular or plural forms. In other words, it should be understood that plural constituents may be a singular constituent or a singular constituent may be plural constituents.

While the embodiments of the present disclosure have been described, those skilled in the art will appreciate that many modifications and changes can be made to the present disclosure without departing from the spirit and essential characteristics of the present disclosure.

Therefore, it should be understood that there is no intent to limit the disclosure to the embodiments disclosed, rather, the disclosure is to cover all modifications, equivalents, and alternatives falling within the spirit and scope of the disclosure as defined by the claims.

FIG. 1 is a diagram for explaining an endoscopic reflection microscope according to an embodiment.

The endoscopic reflection microscope according to an embodiment that will be described below may use an optical fiber bundle-based probe to which a separate lens is not connected, and the probe may be configured in a similar way to an imaging device using ultrasonic waves.

Because the imaging device using ultrasonic waves uses sound waves, the imaging device has arrangement of ultrasonic transducers without using a separate lens, generates ultrasonic waves through each transducer, and measures ultrasonic waves that are reflected back from a target object again using the transducer arrangement.

That is, it is deemed that the endoscopic reflection microscope operates using a similar method to an imaging device using ultrasonic waves except that ultrasonic waves and light are used as waves, respectively, in that the waves are incident on the target object through each optical fiber and waves reflected back from the target object are measured through an optical fiber bundle without using a separate lens.

The endoscopic reflection microscope may correct information on a phase of distorted light based on an optical path difference in optical fibers within the optical fiber bundle, and simultaneously, may also compensate for distortion of information on a phase due to the target object.

The aforementioned phase correction technology according to the present disclosure may also be easily applied to an imaging device using ultrasonic waves, which is configured in a similar way to the endoscopic reflection microscope.

With regard to the imaging device using ultrasonic waves, because the form and structure of biological tissue as a key measurement target are not uniform, phases of the ultrasonic waves are inevitably distorted when the ultrasonic waves are reflected off the target object and are measured through a transducer.

Thus, the imaging device using ultrasonic waves may compensate for distortion of a reflected wave, which occurs in measurement of an image using ultrasonic waves, using the phase correction technology, thereby acquiring a clear image with a high contrast from which speckle noise is removed.

In other words, the present disclosure may also be easily applied to the imaging device using ultrasonic waves because different types of waves are used but very similar structural characteristics in terms of incidence and measurement of the waves are used, and algorithms used to compensate for phase distortion of the waves provide the same effect.

The endoscopic reflection microscope according to an embodiment will be described below in more detail with reference to FIG. 1.

Referring to FIG. 1, an endoscopic reflection microscope 100 according to an embodiment may compensate for phase retardation from an optical fiber bundle in real time without a pre-calibration process.

The endoscopic reflection microscope 100 may acquire an image from which a back-reflection noise component is removed.

The endoscopic reflection microscope 100 may acquire an image in which phase retardation due to the optical fiber bundle is compensated for by accessing the inside of a precision machine or the inside of the human body that a conventional microscope has difficulty in accessing, through an optical fiber bundle-based probe.

The endoscopic reflection microscope 100 may provide a high-resolution image using a reflected wave having the same wavelength as an incident wave without any dyeing for two-photon or fluorescence measurement.

To this end, the endoscopic reflection microscope 100 may include an incident wave output unit 110, a reflected wave receiver 120, and an image acquirer 130.

The incident wave output unit 110 according to an embodiment may output an incident wave from the optical fiber bundle to the target object through any one optical fiber.

For example, the optical fiber bundle may be a probe including a bundle of a plurality of optical fibers, and the diameter of the probe may be set to 300 µm, but may also be set to a size of 150 µm or less.

The optical fiber bundle may receive an incident wave from the incident wave output unit 110 through an incidence plane and may output the incident wave received through an emitting surface.

The reflected wave receiver 120 according to an embodiment may receive the reflected wave output from the target object in response to the output incident wave through a plurality of corresponding optical fibers of the optical fiber bundle.

That is, the reflected wave according to an embodiment may be a signal obtained when an incident wave is reflected by a reflective surface of the target object. In other words, the reflected waves may be backscattered signal waves.

According to an aspect, a plurality of optical fibers for receiving the reflected wave and any one optical fiber for outputting the incident wave may be different optical fibers.

The image acquirer 130 according to an embodiment may establish a reflection matrix corresponding to the reflected wave received through the reflected wave receiver 120 and may acquire an image in which at least one of phase retardation of the incident wave or phase retardation of the reflected wave is compensated for based on the established reflection matrix.

According to an aspect, the target object may be spaced apart from the emitting surface of the optical fiber bundle by a distance of 400 μm to 1,200 μm. The image acquirer 130 may distinguish the raw image between a plurality of pixels on which a reflection data component is concentrated and a pixel on which a back-reflection noise component is concentrated and may physically remove the back-reflection noise component from the pixel on which the back-reflection noise component is concentrated.

For example, the raw image may refer to a raw interference image captured by a camera included in the endoscopic reflection microscope 100 in response to the received reflected wave, and the reflection data component may refer to a data component of the image of the target object. In other words, the reflection data component may refer to data of the backscattered signal waves.

In detail, in the optical fiber bundle, no optical lens or scanner is attached to the emitting surface, and thus, a plurality of optical fibers is exposed, and the target object may be positioned on an out-of-focus plane by being spaced apart from the emitting surface of the optical fiber bundle by a distance of 400 μm to 1,200 μm, differently from the conventional endoscopic microscope in which an optical fiber bundle forms an image pixel. The optical fiber bundle may transmit the reflected wave received through a plurality of optical fibers to the image acquirer 130 according to Fresnel diffraction.

The image acquirer 130 may distinguish the raw image corresponding to the received reflected wave due to the aforementioned configuration of the optical fiber bundle between a plurality of pixels on which the reflection data component is concentrated and a pixel on which the back-reflection noise component is concentrated and may physically separate and remove the back-reflection noise component from the pixel on which the back-reflection noise component is concentrated.

That is, the endoscopic reflection microscope 100 according to an embodiment may overcome a problem in terms of pixelation in an image acquired by a camera when pixelation occurs at a spatial frequency in the acquired image, but not in an actual space and may physically separate and remove the back-reflection noise component due to any one optical fiber for outputting the incident wave.

According to an aspect, the image acquirer 130 may derive a complex field-map based on the raw image corresponding to the reflected wave and may configure a reflection matrix based on the complex field-map.

For example, the image acquirer 130 may derive the complex field-map based on the raw image from which the back-reflection noise component is removed.

According to an aspect, the image acquirer 130 may derive the complex field-map through Hilbert transform of the raw image corresponding to the reflected wave.

According to an aspect, the reflection matrix may refer to a matrix that includes spatial coordinates of the incident wave and spatial coordinates of the reflected wave as a column index and a row index in the optical fiber bundle, respectively and has components of the complex field-map as matrix elements.

According to an aspect, the image acquirer 130 may acquire the image in which phase retardation is compensated for through correlation analysis based on the established reflection matrix.

In detail, the image acquirer 130 may derive a phase retardation component through correlation analysis between columns of the established reflection matrix and may compensate for a phase retardation component of the incident wave in the complex field-map.

The image acquirer 130 may derive a phase retardation component of the reflected wave through correlation analysis between rows of the established reflection matrix and may compensate for the phase retardation component of the phase retardation component of the reflected wave in the complex field-map in which the phase retardation component of the incident wave is compensated for.

According to an aspect, the phase retardation component of the incident wave may be a component obtained by summing the core-dependent phase retardation of the incident wave in the optical fiber bundle and a phase retardation component given by a function of spatial coordinates of the incident wave including a scaling factor.

In other words, the phase retardation component of the incident wave may be a component obtained by performing calculation of the scaling factor and the spatial coordinate component of the incident wave on the core-dependent phase retardation component of the incident wave in the optical fiber bundle.

The phase retardation component of the reflected wave may be a component obtained by performing calculation of the scaling factor and the spatial coordinate component of the reflected wave on the core-dependent phase retardation component of the reflected wave in the optical fiber bundle.

In detail, different phase retardations may occur in the incident wave and the reflected wave due to bending and torsion of the optical fiber during a procedure in which the incident wave and the reflected wave are transmitted through the optical fiber bundle, and occurrence of such phase retardation may cause speckle patterns and loss of image information during image conversion.

Thus, the image acquirer 130 according to an embodiment may detect and compensate for the core-dependent phase retardation component in real time due to bending and torsion of the optical fiber.

The endoscopic reflection microscope according to an embodiment will be described below in detail with reference to FIGS. 2A to 2C FIGS. 2A to 2C are diagrams for explaining an embodiment of an endoscopic reflection microscope according to an embodiment.

In other words, FIGS. 2A to 2C are diagrams for explaining an example of an endoscopic reflection microscope according to an embodiment. Hereinafter, the above description given with reference to FIG. 1 will not be repeated with regard to a description of FIGS. 2A to 2C.

Referring to FIGS. 2A to 2C, reference numeral 210 shows the configuration of an endoscopic reflection microscope according to an embodiment, reference numeral 220 shows an example in which the endoscopic reflection microscope outputs an incident wave to a target object through one optical fiber, and reference numeral 230 shows an example in which the endoscopic reflection microscope receives a reflected wave output from a target object in response to the incident wave through a plurality of optical fibers.

Referring to reference numeral 210, an incident wave output unit may include a laser light source, first to second lenses L1 to L2, fourth to fifth lenses L4 to L5, and a scanning mirror GM.

A reflected wave receiver may include a third lens L3 and a third beam splitter BS3.

The incident wave output unit and the reflected wave receiver may share an optical fiber bundle, an objective lens OL, and a second beam splitter BS2.

The image acquirer may be included in a camera or may be disposed outside the camera and may be operatively associated with the camera.

In detail, the laser light source may be a laser diode having a wavelength A of 532 nm and a coherence length of 6 mm.

A first beam splitter BS1 may split a beam output from the laser light source into a sample beam and a reference beam and may transmit the sample beam and the reference beam to the scanning mirror GM and the third beam splitter BS3, respectively.

The scanning mirror GM may transmit the sample beam to any one optical fiber of the optical fiber bundle and, to this end, a scanning angle may be controlled.

Any one optical fiber that receives the sample beam through the scanning mirror GM in the optical fiber bundle may irradiate the target object with the received sample beam.

The target object may provide the reflected wave corresponding to the radiated sample beam to a plurality of optical fibers of the optical fiber bundle, and the plurality of optical fibers may transmit the received reflected wave to the camera through the objective lens OL and the third beam splitter BS3.

According to an aspect, the third beam splitter BS3 may transmit the reference beam received from the first beam splitter BS1 to the camera, and the camera may generate an interferogram based on the reflected wave and the reference beam.

Referring to reference numerals 220 to 230, $(u_i, v_i)$ may refer to a spatial coordinate component of the incident wave in the optical fiber bundle, and $(u_r, v_r)$ may refer to a spatial coordinate component of the reflected wave in the optical fiber bundle. $\phi_i^b(u_i, v_i)$ may refer to a core-dependent phase retardation component of the incident wave in the optical fiber bundle, and $\phi_r^b(u_r, v_r)$ may refer to a core-dependent phase retardation component of the reflected wave in the optical fiber bundle.

$E_i(x,y)$ may refer to an electric field of an incident wave in the reflective surface SP of the target object, and $E_r(x,y)$ may refer to an electric field of a reflective wave in the reflective surface SP.

$E_{camera}(u_r, v_r)$ may refer to an electric field detected by a camera, and d may refer to a distance between the emitting surface OP of the optical fiber bundle and the reflective surface SP of the target object.

In detail, an incident wave concentrated on the incidence plane IP of any one optical fiber corresponding to the spatial coordinate $(u_i, v_i)$ of the incident wave in the optical fiber bundle may experience core-dependent phase retardation and $\phi_i^b(u_i, v_i)$ and may be output to the target object from the emitting surface OP.

The output incident wave may be in contact with the reflective surface SP of the target object, and in this case, an incident wave $E_i(x, y; u_i, v_i)$ at coordinates (x, y) in contact with the incident wave in the reflective surface SP of the target object may be represented using Expression 1 below.

$$E_i(x, y; u_i, v_i) = \frac{e^{ikd}}{i\lambda d} \exp\left\{i\frac{k}{2d}[(x-u_i)^2 + (y-v_i)^2]\right\} e^{i\phi_i^b(u_i, v_i)}$$ [Expression 1]

Here, k/d may refer to a scaling factor, k may refer to a wavenumber that is $2\pi\lambda^{-1}$, and $\lambda$ may refer to a wavelength of the laser light source.

According to an aspect, the incident wave may be reflected from the reflective surface SP of the target object, which has an amplitude reflectance represented by O(x,y) as an object function, and the reflected wave corresponding to the backscattered signal wave may be transmitted to the optical fiber bundle.

For example, the electric field $E_r(x,y;u_i,v_i)$ of the reflected wave on the reflective surface SP may be derived through calculation of $O(x,y)E_i(x,y;u_i,v_i)$ The reflected wave may be input to the emitting surface OP of a plurality of optical fibers corresponding to the spatial coordinate $(u_r, v_r)$ of the reflected wave through Fresnel diffraction, and the input reflected wave may experience core-dependent phase retardation $\phi_r^b(u_r, v_r)$ and may be transmitted to the camera through the incidence plane IP.

According to an aspect, the image acquirer of the endoscopic reflection microscope according to an embodiment may derive the complex field-map $E_{camera}(u_r, v_r; u_i, v_i)$ based on a raw image corresponding to the transmitted reflected wave, and in this case, the complex field-map $E_{camera}(u_r, v_r; u_i, v_i)$ may be represented using Expression 2 below.

$$E_{camera}(u_r, v_r; u_i, v_i) = -\frac{e^{2ikd}}{\lambda^2 d^2} e^{i\phi_r(u_r, v_r)} \tilde{O}_M\left(\frac{k}{d}(u_r + u_i), \frac{k}{d}(v_r + v_i)\right) e^{i\phi_i(u_i, v_i)}$$ [Expression 2]

Here, $\tilde{O}_M$ may refer to an object spectrum derived b performing Fourier transform on a corrected object function $$O_M(x, y) = O(x, y)\exp\left\{i\frac{k}{d}(x^2 + y^2)\right\},$$

$\phi_i(u_i, v_i)$ may refer to a phase retardation component of the incident wave on an incidence path, and $\phi_r(u_r, v_r)$ may refer to a phase retardation component of the reflected wave on a reflection path.

For example, the incidence path may refer to a path for transmitting the incident wave to the reflective surface SP of the target object from the laser light source in reference numeral 210, and the reflection path may refer to a path for transmitting the reflected wave to the camera from the reflective surface SP of the target object.

In detail, the complex field-map $E_{camera}(u_r, v_r; u_i, v_i)$ may include an object spectrum having spectral shift based on a scaling factor k/d and $(-u_i, -v_i)$, and all quadratic phase terms may be contained in the result of Fresnel diffraction and may be applied to the object function $O_M(x,y)$ in which input and output phase retardations are compensated for.

In general, it is difficult to distinguish the object function $O_M(x,y)$ corrected from the reflected wave, the phase retardation component $\phi_i(u_i,v_i)$ of the incident wave, and the retardation component $\phi_r(u_r,v_r)$ of the reflected wave.

On the other hand, the image acquirer according to an embodiment may easily distinguish between the corrected object function $O_M(x,y)$, the phase retardation component $\phi_i(u_i,v_i)$ of the incident wave, and the phase retardation component $\phi_r(u_r,v_r)$ of the reflected wave using a closed-loop accumulation of single scattering (CLASS) algorithm.

The CLASS algorithm may maximize a single scattering accumulated light signal required to image the target object to optimize the image by numerically finding and compensating for a phase change of a wavefront of light for each angle based on a time-resolution reflection matrix.

Hereinafter, an example in which an image acquirer according to an embodiment acquires an image formed by compensating for phase retardation using the CLASS algorithm will be described in more detail. In addition, the entire process described below may be repeated multiple times to compensate for phase retardation.

First, the image acquirer may establish a reflection matrix R based on the complex field-map $E_{camera}(u_r,v_r;u_i,v_i)$.

For example, the reflection matrix R may be a matrix that includes spatial coordinates $(u_i,v_i)$ of the incident wave and spatial coordinates $(u_r,v_r)$ of the reflected wave as a column index and a row index, respectively and has components of the complex field-map $E_{camera}(u_r,v_r;u_i,v_i)$ as matrix elements.

Then, the image acquirer may automatically distinguish between the phase retardation component $\phi_i(u_i,v_i)$ of the incident wave and the phase retardation component $\phi_r(u_r,v_r)$ of the reflected wave, for acquiring the corrected object function $O_M(x,y)$, through correlation analysis between columns and rows of the established reflection matrix R.

The image acquirer may acquire a reflectance map of the target object through a relationship such as $|O_M(x,y)|^2=|O(x,y)|^2$ and may automatically identify a quadratic phase term such as $$\frac{k}{2d}(u_i^2 + v_i^2)$$

for an object within a scope of work.

The image acquirer may acquire a distance d between the emitting surface OP of the optical fiber bundle and the reflective surface SP of the target object from the quadratic phase term, and thus may also re-establish a 3D image from recording of a single reflection matrix.

In detail, the image acquirer may derive a phase retardation component $\phi_i(u_i,v_i)$ of the incident wave through correlation analysis between columns of the reflection matrix R and may compensate for the phase retardation component $\phi_i(u_i,v_i)$ of the incident wave in the complex field-map $E_{camera}(u_r,v_r;u_i,v_i)$.

According to an aspect, the phase retardation component $\phi_i(u_i,v_i)$ of the incident wave may be derived using Expression 3 below for performing calculation of a scaling factor k/d and the spatial coordinate component $(u_i,v_i)$ of the incident wave on the core-dependent phase retardation component $\phi_i^b(u_i,v_i)$ of the incident wave.

$$\phi_i(u_i, v_i) = \frac{k}{2d}(u_i^2 + v_i^2) + \phi_i^b(u_i, v_i) \quad [\text{Expression 3}]$$

The image acquirer may derive the complex field-map $E_1(u_r,v_r;u_i,v_i)$ in which the phase retardation component of the incident wave is compensated for through Expression 4 below.

$$E_1(u_r,v_r;u_i,v_i)=e^{-i\phi_i(u_i,v_i)}E_{camera}(u_r,v_r;u_i,v_i) \quad [\text{Expression 4}]$$

Then, the image acquirer may derive the phase retardation component $\phi_r(u_r,v_r)$ of the reflected wave through correlation analysis between rows of the reflection matrix R and may compensate for the phase retardation component $\phi_r(u_r,v_r)$ of the reflected wave in the complex field-map $E_1(u_r,v_r;u_i,v_i)$ in which the phase retardation component of the incident wave is compensated for.

According to an aspect, the phase retardation component $\phi_r(u_r,v_r)$ of the reflected wave may be derived using Expression 5 below for calculation of the scaling factor k/d and the spatial coordinate component $(u_r,v_r)$ of the reflected wave on the core-dependent phase retardation component $\phi_i^b(u_r,v_r)$ of the reflected wave.

$$\phi_r(u_r, v_r) = \frac{k}{2d}(u_r^2 + v_r^2) + \phi_r^b(u_r, v_r) \quad [\text{Expression 5}]$$

The image acquirer may derive a complex field-map $E_2(u_r,v_r;u_i,v_i)$ in which phase retardation of the reflected wave is compensated for using Expression 6.

$$E_2(u_r,v_r;u_i,v_i)=e^{-i\phi_i(u_i,v_i)}E_{camera}(u_r,v_r;u_i,v_i) \quad [\text{Expression 6}]$$

According to an aspect, the image acquirer ma repeat the aforementioned process until the object spectrum $$\tilde{O}_M\left(\frac{k}{d}(u_r + u_i), \frac{h}{d}(v_r + v_i)\right)$$

is identified.

In detail, the image acquirer may move an object spectrum corresponding to each of a plurality of images (complex field-map) by spatial coordinates $(u_i,v_i)$ of the incident wave, which means conversion of the object spectrum for all optical fibers for outputting the incident wave in the optical fiber bundle.

The image acquirer may sum the converted object spectrums and may perform inverse Fourier transform to derive the corrected object function $O_M(x,y)$.

That is, the image acquirer according to an embodiment may acquire an image in which phase retardation is compensated for in real time by identifying and compensating for the phase retardation component $\phi_i(u_i,v_i)$ of the incident wave and the phase retardation component $\phi_r(u_r,v_r)$ of the reflected wave through correlation analysis between columns and rows of the reflection matrix R.

FIG. 3 is a diagram for explaining an example of outputting an incident wave through an optical fiber bundle according to an embodiment.

Referring to FIG. 3, reference numeral 300 shows a bright-field image in an incidence plane of an optical fiber bundle when an incoherent source is illuminated on an emitting surface of an optical fiber bundle.

Referring to reference numeral 300, the endoscopic reflection microscope according to an embodiment may select any one optical fiber for outputting an incident wave (sample beam) to the target object in the optical fiber bundle, and in detail, the endoscopic reflection microscope may control an angle of the scanning mirror to concentrate the sample beam on any one optical fiber core.

FIGS. 4A to 4H are diagrams for explaining an example of deriving a complex field-map through an endoscopic reflection microscope according to an embodiment.

Referring to FIGS. 4A to 4H, FIGS. 4A to 4D show row images acquired from reflected waves corresponding to incident waves having spatial coordinates $(u_i, v_i)$ of (0 µm, 0 µm), (−31 µm, −11 µm), (37 µm, 45 µm), and (−62 µm, 89 µm), respectively, and FIGS. 4E to 4H show images of a complex field-map corresponding to the raw images of FIGS. 4A to 4D, respectively.

Referring to FIGS. 4A to 4D, spatial coordinates of raw images corresponding to reflected waves may correspond to spatial coordinates of reflected waves in a plurality of optical fibers, and the brightest pixel thereof may refer to a pixel on which a back-reflection noise component due to one optical fiber for outputting the incident wave is concentrated.

In detail, in the optical fiber bundle, no optical lens or scanner is attached to the emitting surface, and thus, a plurality of optical fibers is exposed, and the target object may be positioned on an out-of-focus plane by being spaced apart from the emitting surface of the optical fiber bundle by a distance of 400 µm to 1,200 µm, differently from the conventional endoscopic reflection microscope in which an optical fiber bundle forms an image pixel.

The endoscopic reflection microscope according to an embodiment may distinguish the raw image corresponding to the received reflected wave due to the aforementioned configuration of the optical fiber bundle between a plurality of pixels on which the reflection data component is concentrated and a pixel on which the back-reflection noise component is concentrated and may physically separate and remove the back-reflection noise component from the distinguished pixel.

The endoscopic reflection microscope according to an embodiment may derive the complex field-map shown in FIGS. 4E to 4H by performing Hilbert transform on the raw image from which the back-reflection noise component is physically separated in FIGS. 4A to 4D.

FIGS. 5A to 5F are diagrams for explaining an example of acquiring an image through an endoscopic reflection microscope according to an embodiment. FIGS. 6A to 6D are diagrams for explaining an example of identifying phase retardation through an endoscopic reflection microscope according to an embodiment.

Referring to FIGS. 5A to 6D, FIGS. 5A and 5D show images of target objects with high and low reflectance contrasts of a target with respect to a background acquired through an endoscopic reflection microscope based on a conventional image acquisition method, respectively, FIGS. 5B and 5E show images on which inverse Fourier transform is performed on a spectrum in which phase retardation of an incident wave and phase retardation of a reflected wave are not compensated for in a complex field-map for a target object with a high reflectance contrast and a target object with a low reflectance contrast, and FIGS. 5C and 5F show images in which phase retardation of an incident wave and phase retardation of a reflected wave are compensated for in a complex field-map for a target object with a high reflectance contrast and a target object with a low reflectance contrast.

FIGS. 6A and 6C show a phase retardation component $\phi_i(u_i, v_i)$ of an incident wave for acquiring the images of the target objects with high and low reflectance contrasts of a target with respect to a background shown in FIG. 5, respectively, and FIGS. 6B and 6D show a phase retardation component $\phi_r(u_r, v_r)$ of a reflected wave for acquiring images of target objects with high and low reflectance contrasts of a target with respect to a background, respectively.

In detail, it may be seen that the images on which inverse Fourier transform is performed as shown in FIGS. 5B and 5E may cause speckle patterns and image information may be lost.

On the other hand, the endoscopic reflection microscope according to an embodiment may acquire an image without pixelation and having high quality and high-resolution as shown in FIG. 5C compared with an image of the conventional endoscopic reflection microscope (refer to FIGS. 5A and 5D) by distinguishing between the phase retardation component $\phi_i(u_i, v_i)$ of the incident wave and the phase retardation component $\phi_r(u_r, v_r)$ of the reflected wave using the CLASS algorithm described with reference to FIG. 2 and compensating for the distinguished components in the complex field-map.

The resolution of the endoscopic reflection microscope according to an embodiment may be determined depending on a diameter D of an optical fiber bundle in a numerical aperture (NA) set to $\alpha = n(D/2)d^{-1}$, and here, n may refer to a refractive index between an optical fiber and a target object. When the resolution a is greater than a numerical aperture (NA) of 0.4 of the optical fiber itself, a spatial resolution may be limited.

In detail, as the distance d decreases to 400 µm from 1,200 µm, $\alpha$ may increase to 0.47 from 0.12 for n=1, and theoretical spatial resolving power may increase to 0.67 µm from 1.6 µm.

A view field diameter of the endoscopic reflection microscope according to an embodiment may be set to $L = (\lambda/n) d\lambda D^{-1}$, and here, a distance $\Delta D$ between optical fiber cores may be set to 3.2 µm. That is, as the distance d increases, the view field diameter L may increase to 170 µm from 66 µm.

A distance $D_{eff}$ between effective optical fiber cores in the endoscopic reflection microscope according to an embodiment may decrease to 1.5 µm due to a synthesis process of a plurality of images. Thus, as the distance d increases, a range of the view field diameter L may be 140 µm to 410 µm. It may be seen that a view field diameter L estimated at the distance d=500 µm is 170 µm and this is consistent with the experimental result.

In the target object with a low reflectance contrast of a target with respect to a background of FIG. 5D acquired through the conventional endoscopic reflection microscope, back-reflection noise is much stronger than backscattered signal waves, and thus it may be seen that it is impossible to clearly identify the target object.

On the other hand, in the image of the target object with a low reflectance contrast of a target with respect to a background of FIG. 5F acquired through the endoscopic reflection microscope according to an embodiment, it may be seen that the target object is clearly identified by removing back-reflection noise and compensating for a phase retardation component of the incident wave and a phase retardation component of the reflected wave.

FIGS. 7A to 7B are diagrams for explaining an example of acquiring an image of a target object positioned in a narrow and curved path using an endoscopic reflection microscope according to an embodiment.

Referring to FIGS. 7A to 7B, FIG. 7A shows an image of a target object acquired using a general endoscopic reflection microscope, and FIG. 7B shows an image of a target object acquired using an endoscopic reflection microscope according to an embodiment.

In detail, FIGS. 7A to 7B shows acquired images of target objects obtained by inserting an optical fiber bundle (probe)

into a plastic tube having a curved path with an inner diameter of 10 mm and an outer diameter of 15 mm and a length of 80 cm.

As seen from FIG. 7A, pixelation may occur in an image of a target object acquired using a general endoscopic reflection microscope, and an image with low resolution may be output as the image of the target object. On the other hand, as seen from FIG. 7B, a clear image without pixelation may be output as an image of a target object acquired using the endoscopic reflection microscope according to an embodiment.

In other hand, it may be seen that the endoscopic reflection microscope according to an embodiment may acquire a high-resolution image without a fluorescent label even if a target object is positioned in a narrow and curved path.

FIG. 8 is a diagram for explaining an experimental process of acquiring an image by adjusting a focal length by an endoscopic reflection microscope according to an embodiment. FIGS. 9A to 9D are diagrams for explaining an example of acquiring an image through the experimental process by an endoscopic reflection microscope according to an embodiment.

Referring to FIGS. 8 to 9D, reference numeral 800 shows an experimental process of acquiring an image with respect to two target objects positioned at different depths A and B by the endoscopic reflection microscope according to an embodiment.

FIGS. 9A and 9B show images acquired at depths A and B through an objective lens, respectively and FIGS. 9C and 9D show images acquired at depths A and B which are re-established based on a reflection matrix by an endoscopic reflection microscope according to an embodiment, respectively.

In detail, in order to determine the validity of an image acquired through an endoscopic reflection microscope according to an embodiment, transmission images may be captured by adjusting a focal point to different depths (depths A and B) like the images shown in FIGS. 9A and 9B and may be collected by an objective lens using a wavelength transmitted through the target object, and the endoscopic reflection microscope according to an embodiment may have an effective numerical aperture (NA) of 0.3 that is higher than a numerical aperture (NA) of 0.1 of the objective lens, and thus it may be seen that the corresponding image has excellent characteristics compared with the transmission image acquired through the objective lens.

The endoscopic reflection microscope according to an embodiment may derive a complex field-map and may then implement 3D imaging.

The endoscopic reflection microscope according to an embodiment may apply a single reflection matrix set for two target objects stacked at different depths A and B at an interval of 200 μm, and as shown in FIG. 9D, a reflective image at the depth B provides a stronger relationship for calculating core-dependent phase retardation, and thus a target image at the depth B may be clearly identified.

A target image at the depth A may be clearly identified as shown in FIG. 9C by adding a phase for changing a focal length to a reflection matrix in which phase retardations of the incident and reflected waves are compensated for with respect to the depth B.

FIGS. 10A to 10C are diagrams for explaining an example of acquiring an image of biological tissue that is not dyed through an endoscopic reflection microscope according to an embodiment.

Referring to FIGS. 10A to 10C, FIG. 10A shows a transmission image of biological tissue, acquired through an objective lens, FIG. 10B shows an image of biological tissue, acquired through a general endoscopic reflection microscope, and FIG. 10C shows an image of biological tissue, acquired through an endoscopic reflection microscope according to an embodiment. For example, the biological tissue may be a tissue including the villi of a mouse.

In detail, as seen from FIGS. 10A to 10C, the villi may not be identified due to a very low contrast between a target and a background and only shadows may be displayed vaguely in the image acquired through the general endoscopic reflection microscope. On the other hand, the villi may be clearly identified because there is no back-reflection noise and phase retardation in the image acquired through the endoscopic reflection microscope according to an embodiment.

FIG. 11 is a diagram for explaining an image acquisition method using an endoscopic reflection microscope according to an embodiment.

In other words, FIG. 11 is a diagram for explaining a method of operating the endoscopic reflection microscope according to an embodiment described above with reference to FIGS. 1 to 10C Hereinafter, the above description given with reference to FIGS. 1 to 10C will not be repeated with regard to a description of FIG. 11.

Referring to FIG. 11, in operation 1110 of the image acquisition method according to an embodiment, an incident wave output unit may output an incident wave to a target object through any one optical fiber in an optical fiber bundle.

Then, in operation 1120 of the image acquisition method according to an embodiment, a reflected wave receiver may receive a reflected wave output from the target object in response to the incident wave through a plurality of corresponding optical fibers in the optical fiber bundle.

Then, in operation 1130 of the image acquisition method according to an embodiment, an image acquirer may establish a reflection matrix corresponding to the reflected wave and may acquire an image in which at least one of phase retardation of the incident wave or phase retardation of the reflected wave is compensated for based on the established reflection matrix.

As a result, according to the present disclosure, phase retardation due to an optical fiber bundle may be compensated for in real time without a pre-calibration process.

According to the present disclosure, an image from which a back-reflection noise component is removed may be acquired.

According to the present disclosure, an image in which phase retardation due to the optical fiber bundle is compensated for may be acquired by accessing the inside of a precision machine or the inside of the human body that a conventional microscope has difficulty in accessing, through an optical fiber bundle-based probe.

According to the present disclosure, a high-resolution image may be provided using a reflected wave having the same wavelength as an incident wave without any dyeing for two-photon or fluorescence measurement.

The present disclosure relates to an endoscopic reflection microscope for imaging a target object positioned on a narrow and curved path without a fluorescent label, and no optical lens or scanner is attached to an emitting surface of the optical fiber bundle, and thus, the thinnest probe may be implemented.

According to an embodiment of the present disclosure, phase retardation due to an optical fiber bundle may be compensated for in real time without a pre-calibration process.

According to the present disclosure, an image from which a back-reflection noise component is removed may be acquired.

According to the present disclosure, an image in which phase retardation due to the optical fiber bundle is compensated for may be acquired by accessing the inside of a precision machine or the inside of the human body that a conventional microscope has difficulty in accessing, through an optical fiber bundle-based probe.

According to the present disclosure, a high-resolution image may be provided using a reflected wave having the same wavelength as an incident wave without any dyeing for two-photon or fluorescence measurement.

Although exemplary embodiments of the present disclosure have been disclosed for illustrative purposes, those skilled in the art will appreciate that various modifications, additions and substitutions are possible, without departing from the scope and spirit of the disclosure as disclosed in the accompanying claims. For example, a proper result may be achieved even if the techniques described above are implemented in an order different from that for the disclosed method, and/or disclosed constituents such as a system, structure, device and circuit are coupled to or combined with each other in a form different from that for the disclosed method or replaced by other constituents or equivalents.

It should be understood, however, that there is no intent to limit the disclosure to the embodiments disclosed, rather, the disclosure is to cover all modifications, equivalents, and alternatives falling within the spirit and scope of the disclosure as defined by the claims.

What is claimed is:

1. An endoscopic reflection microscope comprising:
   an incident wave output unit configured to output an incident wave to a target object through any one optical fiber in an optical fiber bundle;
   a reflected wave receiver configured to receive a reflected wave output from the target object in response to the incident wave through a plurality of corresponding optical fibers in the optical fiber bundle; and
   an image acquirer configured to establish a reflection matrix corresponding to the reflected wave and to acquire an image in which at least one of phase retardation of the incident wave or phase retardation of the reflected wave is compensated for based on the established reflection matrix.

2. The endoscopic reflection microscope according to claim 1, wherein:
   the target object is spaced apart from an emitting surface of the optical fiber bundle by a distance of 400 µm to 1,200 µm; and
   the image acquirer distinguishes a raw image corresponding to the reflected wave between a plurality of pixels on which a reflection data component is concentrated and a pixel on which a back-reflection noise component is concentrated and physically removes the back-reflection noise component from the pixel on which the back-reflection noise component is concentrated.

3. The endoscopic reflection microscope according to claim 1, wherein the image acquirer derives a complex field-map based on the raw image corresponding to the reflected wave and establishes the reflection matrix based on the complex field-map.

4. The endoscopic reflection microscope according to claim 3, wherein the reflection matrix is a matrix including spatial coordinates of the incident wave and spatial coordinates of the reflected wave as a column index and a row index in the optical fiber bundle, respectively and having components of the complex field-map as matrix elements.

5. The endoscopic reflection microscope according to claim 3, wherein the image acquirer acquires the image in which phase retardation is compensated for through correlation analysis based on the established reflection matrix.

6. The endoscopic reflection microscope according to claim 3, wherein the image acquirer derives a phase retardation component of the incident wave through correlation analysis between columns of the established reflection matrix and compensates for the phase retardation component of the incident wave in the complex field-map.

7. The endoscopic reflection microscope according to claim 6, wherein the phase retardation component of the incident wave is a component obtained by performing calculation of a scaling factor and the spatial coordinate component of the incident wave on a core-dependent phase retardation component of the incident wave in the optical fiber bundle.

8. The endoscopic reflection microscope according to claim 6, wherein the image acquirer derives a phase retardation component of the reflected wave through correlation analysis between rows of the established reflection matrix and compensates for the phase retardation component of the reflected wave in the complex field-map in which the phase retardation component of the incident wave is compensated for.

9. The endoscopic reflection microscope according to claim 8, wherein the phase retardation component of the reflected wave is a component obtained by performing calculation of a scaling factor and the spatial coordinate component of the reflected wave on a core-dependent phase retardation component of the reflected wave in the optical fiber bundle.

10. The endoscopic reflection microscope according to claim 3, wherein the image acquirer derives the complex field-map through Hilbert transform on the raw image corresponding to the reflected wave.

11. An image acquisition method using an endoscopic reflection microscope, the method comprising:
    outputting an incident wave to a target object through any one optical fiber in an optical fiber bundle, by an incident wave output unit;
    receiving a reflected wave output from the target object in response to the incident wave through a plurality of corresponding optical fibers in the optical fiber bundle, by a reflected wave receiver; and
    establishing a reflection matrix corresponding to the reflected wave and acquiring an image in which at least one of phase retardation of the incident wave or phase retardation of the reflected wave is compensated for based on the established reflection matrix, by an image acquirer.

* * * * *